United States Patent [19]
Aulbach et al.

[11] Patent Number: 5,831,105
[45] Date of Patent: Nov. 3, 1998

[54] PROCESS FOR PREPARING BRIDGED METALLOCENES

[75] Inventors: Michael Aulbach, Hofheim; Frank Küber, Oberursel, both of Germany

[73] Assignee: Targor GmbH, Germany

[21] Appl. No.: 532,514

[22] Filed: Sep. 22, 1995

[30] Foreign Application Priority Data

Sep. 28, 1994 [DE] Germany ............ 44 34 640.9

[51] Int. Cl.⁶ ............... C07F 17/00; C07F 7/00; C07F 19/00
[52] U.S. Cl. ............... 556/11; 556/7; 556/8; 556/1; 556/12; 556/20; 556/28; 556/58; 534/15; 526/943; 502/103; 502/117
[58] Field of Search ............ 556/11, 12, 20, 556/28, 7, 8, 1, 27, 43, 53, 58; 534/15; 526/943; 502/103, 117

[56] References Cited

U.S. PATENT DOCUMENTS

| | | | |
|---|---|---|---|
| 5,017,714 | 5/1991 | Welborn, Jr. | 556/12 |
| 5,145,819 | 9/1992 | Winter et al. | 502/117 |
| 5,304,614 | 4/1994 | Winter et al. | 527/127 |
| 5,324,800 | 6/1994 | Welborn, Jr. et al. | 526/160 |
| 5,453,221 | 9/1995 | Lisowsky et al. | 260/665 G |
| 5,543,535 | 8/1996 | Lisowsky et al. | 556/11 |

FOREIGN PATENT DOCUMENTS

| | | |
|---|---|---|
| 1319784 | 6/1993 | Canada . |
| 1319785 | 6/1993 | Canada . |
| 0 129 368 B1 | 12/1984 | European Pat. Off. . |
| 0 336 127 B1 | 10/1989 | European Pat. Off. . |
| 0 336 128 B1 | 10/1989 | European Pat. Off. . |
| 0 344 887 A2 | 12/1989 | European Pat. Off. . |
| 0 485 823 B1 | 5/1992 | European Pat. Off. . |
| 537 686A1 | 4/1993 | European Pat. Off. . |
| 44 06 109A1 | 8/1995 | Germany . |
| 44 06 110A1 | 8/1995 | Germany . |

OTHER PUBLICATIONS

Spaleck et al., "The Influence of Aromatic Substituents on the Polymerization Behavior of Bridged Zirconocene Catalysts", Organometallics 1994, 13, 954–963.

*Primary Examiner*—Porfirio Nazario-Gonzalez
*Attorney, Agent, or Firm*—Connolly & Hutz

[57] ABSTRACT

In-situ process for preparing a bridged metallocene, which comprises reacting a substituted cyclopentadiene A, if desired an unsubstituted or substituted cyclopentadienyl compound B, at least one base, at least one bridging reagent and at least one metal component with one another.

13 Claims, No Drawings

PROCESS FOR PREPARING BRIDGED METALLOCENES

The present invention relates to an in-situ process for preparing bridged metallocenes which can be used as catalyst components for olefin polymerization.

Bridged metallocenes are used, particularly together with aluminoxane as highly active catalyst components in olefin polymerization (EP 129 368). Use is here made, in particular, of silicon-bridged and germanium-bridged metallocenes (EP 336 127, EP 336 128, EP 485 823). The synthesis of these metallocenes is carried out as described in the literature in a two-stage synthesis (Organomet. 1994, 13, 954–963; ibid, 964–970). In the first stage, the bridged ligand system is built up by reacting two equivalents of an unsubstituted or substituted cyclopentadiene with a bridging reagent such as dialkyldichlorosilane, dialkyldichlorogermane or 1,2-dibromethane. This is isolated and in the subsequent second stage, after deprotonation with strong bases, reacted with metal compounds such as $TiCl_4$, $ZrCl_4$, $Zr(NMe_2)_4$ to give a bridged metallocene. A disadvantage of this two-stage synthesis is that, to isolate the bridged ligand system, the reaction mixture has to be worked up and the bridged ligand system has to subsequently be purified by crystallization or chromatography, which involves additional work and cost.

EP 344 887 describes a process for preparing a silicon-bridged metallocene, with the reaction being carried out in three different reaction vessels. In addition, the transition metal component $ZrCl_4 \cdot 2THF$ has to be prepared separately at very low temperatures.

It is an object of the invention to develop a simple and inexpensive process for preparing bridged metallocenes, which avoids the disadvantages known from the prior art.

It has surprisingly been found that this object is achieved by a technically simple to handle, in-situ process in which a substituted cyclopentadiene is reacted in situ to give a bridged metallocene.

The present invention accordingly provides an in-situ process for preparing a bridged metallocene, which comprises reacting a substituted cyclopentadiene A, if desired a cyclopentadienyl compound B, at least one base, at least one bridging reagent and at least one metal component with one another.

In the in-situ process of the invention, the following steps are preferably carried out in succession:
a) a substituted cyclopentadiene A is deprotonated with a base and then reacted with a bridging reagent,
b) if desired, a second, unsubstituted or substituted cyclopentadienyl compound B which has a substitution pattern different from the cyclopentadiene A is added, and
c) a base is again added and then a metal component is added.

To prepare bridged metallocenes having identical cyclopentadienyl ligands, a preferred embodiment of the in-situ process of the invention comprises deprotonating a substituted cyclopentadiene A with a base and then reacting it with a bridging reagent to give a bridged ligand system which is subsequently, without isolation of the bridged ligand system, again deprotonated with a base and reacted with a metal component to give a bridged metallocene.

The substituted cyclopentadiene A used in the process of the invention preferably has the formula Ia

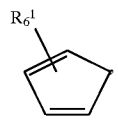

where the radicals
$R^1$ are identical or different and are each a hydrogen atom, a halogen atom, a $C_1$–$C_{30}$-hydrocarbon group such as a $C_1$–$C_{25}$-alkyl group which may be linear, branched, cyclic or substituted cyclic, a $C_1$–$C_{15}$-alkylalkenyl, $C_6$–$C_{24}$-aryl or $C_7$–$C_{30}$-arylalkyl group, or a $C_1$–$C_{12}$-alkoxy group, or two or more adjacent radicals $R^1$ can form a $C_4$–$C_{24}$-ring system which in turn can be substituted, or an $R'_3Si$ group where $R'$ are identical or different and are each a hydrogen atom, a halogen atom, a $C_1$–$C_{20}$-alkyl, a $C_1$–$C_{10}$-fluoroalkyl, a $C_1$–$C_{10}$-alkoxy, a $C_6$–$C_{14}$-aryl, a $C_6$–$C_{10}$-fluoroaryl, a $C_6$–$C_{10}$-aryloxy, a $C_2$–$C_{10}$-alkenyl, a $C_7$–$C_{40}$-arylalkyl, a $C_7$–$C_{40}$-alkylaryl or a $C_8$–$C_{40}$-arylalkenyl group, where at least two radicals $R^1$ are hydrogen atoms and at least one radical $R^1$ is different from a hydrogen atom.

The substituted cyclopentadiene A of the formula Ia preferably bears one or more $C_1$–$C_{30}$-hydrocarbon radicals as substituents. Examples of such cyclopentadienes A of the formula I are 2-methylcyclopentadiene, methyl-tert-butylcyclopentadiene, tert-butylcyclopentadiene, isopropylcyclopentadiene, dimethylcyclopentadiene, trimethylethylcyclopentadiene, 5-phenylcyclopentadiene, diphenylcyclopentadiene, indene, 2-methylindene, 2-ethylindene, 3-methylindene, 3-tert-butylindene, 2-methyl-4-phenylindene, 2-ethyl-4-phenylindene, 2-methyl-4-naphthylindene, 2-methyl-4-isopropylindene, benzoindene, 2-methyl-4,5-benzoindene, 2-methyl-α-acenaphthindene, 2-methyl-4,6-diisopropylindene, fluorene, 4methylfluorene or 2,7-di-tert-butylfluorene. Particular preference is given to indene derivatives. Preferably, the indene derivatives bear a $C_1$–$C_{10}$-hydrocarbon radical such as $C_1$–$C_{10}$-alkyl on the five-membered ring, particularly in the 2 position, and on the six-membered ring are either unsubstituted or bear one or more $C_1$–$C_{20}$-hydrocarbon radicals such as $C_1$–$C_{10}$-alkyl, $C_6$–$C_{20}$-aryl (e.g. phenyl or naphthyl) or two or more of the $C_1$–$C_{20}$-hydrocarbon radicals form a ring system.

The unsubstituted or substituted cylopentadienyl compound B which may be used if desired preferably has the formula Ib

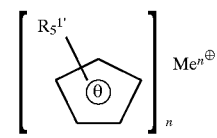

where the radicals
$R^{1'}$ are identical or different and are each a hydrogen atom, a halogen atom, a $C_1$–$C_{30}$-hydrocarbon group such as a $C_1$–$C_{25}$-alkyl group which may be linear, branched, cyclic or substituted cyclic, a $C_1$–$C_{15}$-alkylalkenyl, $C_6$–$C_{24}$-aryl or $C_7$–$C_{30}$-arylalkyl group, or a $C_1$–$C_{12}$-alkoxy group, or two or more adjacent radicals $R^{1'}$ can form a $C_4$–$C_{24}$-ring system which can in turn be substituted, or an $R'_3Si$ group, where $R'$ can be identical or different and are each a hydrogen atom, a halogen atom, a $C_1$–$C_{20}$-alkyl, a $C_1$–$C_{10}$-fluoroalkyl, a $C_1$–$C_{10}$-alkoxy, a $C_6$–$C_{14}$-aryl, a $C_6$–$C_{10}$-fluoroaryl, a $C_6$–$C_{10}$-aryloxy, a $C_2$–$C_{10}$-alkenyl, a $C_7$–$C_{40}$-arylalkyl, a $C_7$–$C_{40}$-alkylaryl or a $C_8$–$C_{40}$-arylalkenyl group, where at least one radical $R^1$ is a hydrogen atom and Me is an n-valent metal and n is equal to 1 or 2. Me is preferably an alkali metal such as lithium, sodium or potassium or an alkaline earth metal such as magnesium.

The cyclopentadienyl group of the cyclopentadienyl compound B of the formula Ib is preferably substituted and preferably bears as substituents one or more $C_1$–$C_{30}$-hydrocarbon radicals. Examples of such cyclopentadienyl groups are 2-methylcyclopentadienyl, methyl-tert-butylcyclopentadienyl, tert-butylcyclopentadienyl, isopropylcyclopentadienyl, dimethylcyclopentadienyl, trimethylethylcyclopentadienyl, 5-phenylcyclopentadienyl, diphenylcyclopentadienyl, indenyl, 2-methylindenyl, 2-ethylindenyl, 3-methylindenyl, 3-tert-butylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl. Particular preference is given to indenyl derivatives. Preferably, the indenyl derivatives bear a $C_1$–$C_{10}$-hydrocarbon radical such as $C_1$–$C_{10}$-alkyl on the five-membered ring, particularly in the 2 position, and on the six-membered ring are either unsubstituted or bear one or more $C_1$–$C_{20}$-hydrocarbon radicals such as $C_1$–$C_{10}$-alkyl, $C_6$–$C_{20}$-aryl (e.g. phenyl or naphthyl) or two or more of the $C_1$–$C_{20}$-hydrocarbon radicals form a ring system.

Bridging reagents used are preferably compounds of the formula $ZY_n$, where Z is

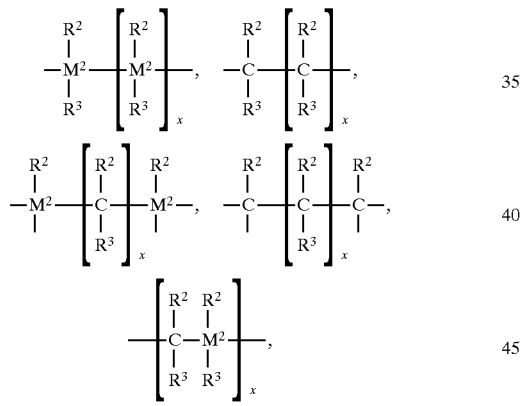

$=BR^2$, $=AlR^2$, —Ge—, —O—, —S—, $=SO$, $=SO_2$, $=NR^2$, $=CO$, $=PR^2$ or $=P(O)R^2$, where $R^2$ and $R^3$ are identical or different and are each a hydrogen atom, a halogen atom, a $C_1$–$C_{20}$-alkyl, a $C_1$–$C_{10}$-fluoroalkyl, a $C_1$–$C_{10}$-alkoxy, a $C_6$–$C_{14}$-aryl, a $C_6$–$C_{10}$-fluoroaryl, a $C_6$–$C_{10}$-aryloxy, a $C_2$–$C_{10}$-alkenyl, a $C_7$–$C_{40}$-arylalkyl, a $C_7$–$C_{40}$-alkylaryl or a $C_8$–$C_{40}$-arylalkenyl group, or two or more radicals $R^2$ and $R^3$ together with the atoms connecting them form one or more rings, $M^2$ are identical or different and are each silicon, germanium or tin, x is an integer from zero to 18, Y are identical or different and are each a leaving group such as a halogen atom or a tosylate, and n is equal to 2 or 4.

Bases preferably used are alkyl-alkali metal compounds such as alkyllithium compounds, e.g. methyllithium and butyllithium, but it is also possible to use pure metals such as lithium and sodium. In principle, it is possible to use all bases which are able to deprotonate the CH acid cyclopentadienes or cyclopentadienyls such as substituted cyclopentadiene/cyclopentadienyl, substituted or unsubstituted indene/indenyl or substituted or unsubstituted fluorene/fluorenyl.

Metal components preferably used in the process of the invention are compounds of the formula $MX_p$, where M is a metal of group IIIb, IVb, Vb, VIb of the Periodic Table of the Elements, X is a halogen atom or an $NR''_2$ group, where $R''$ are identical or different and are each a hydrogen atom, a halogen atom or a $C_1$–$C_{40}$-carbon-containing group such as a $C_1$–$C_{20}$-alkyl, a $C_1$–$C_{10}$-fluoroalkyl, a $C_1$–$C_{10}$-alkoxy, a $C_6$–$C_{14}$-aryl, a $C_6$–$C_{10}$-fluoroaryl, a $C_6$–$C_{10}$-aryloxy, a $C_2$–$C_{10}$-alkenyl, a $C_7$–$C_{40}$-arylalkyl, a $C_7$–$C_{40}$-alkylaryl or a $C_8$–$C_{40}$-arylalkenyl group, and p is an integer from 2 to 6.

In the in-situ process of the invention, preference is given to preparing bridged metallocenes of the formula II

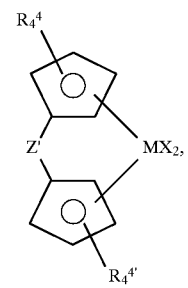

where $R^4$ and $R^{4'}$ are identical or different and are each a hydrogen atom, a halogen atom, a $C_1$–$C_{30}$-hydrocarbon group such as $C_1$–$C_{25}$-alkyl, e.g. $C_4$–$C_{12}$-cycloalkyl, which in turn can bear a $C_1$–$C_{12}$-alkyl as substituent, $C_1$–$C_{15}$-alkylalkenyl, $C_6$–$C_{24}$-aryl, $C_7$–$C_{30}$-arylalkyl, $C_1$–$C_{12}$-alkoxy, or two or more adjacent radicals together can form a $C_4$–$C_{24}$-ring system which can in turn be substituted, an $R'_3Si$ group, where $R'$ are identical or different and are each a hydrogen atom, a halogen atom, a $C_1$–$C_{20}$-alkyl, a $C_1$–$C_{10}$-fluoroalkyl, a $C_1$–$C_{10}$-alkoxy, a $C_6$–$C_{14}$-aryl, a $C_6$–$C_{10}$-fluoroaryl, a $C_6$–$C_{10}$-aryloxy, a $C_2$–$C_{10}$-alkenyl, a $C_7$–$C_{40}$-arylalkyl, a $C_7$–$C_{40}$-alkylaryl or a $C_8$–$C_{40}$-arylalkenyl group, and $R^4$ and $R^{4'}$ can be connected to $Z'$, $Z'$ is

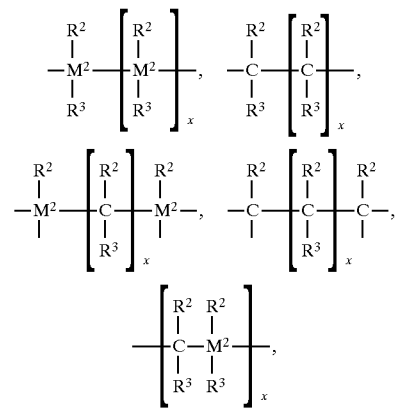

$=BR^2$, $=AlR^2$, —Ge—, —O—, —S—, $=SO$, $=SO_2$, $=NR^2$, $=CO$, $=PR^2$ or $=P(O)R^2$, where $R^2$ and $R^3$ are identical or different and are each a hydrogen atom, a halogen atom, a $C_1$–$C_{20}$-alkyl, a $C_1$–$C_{10}$-fluoroalkyl, a $C_1$–$C_{10}$-alkoxy, a $C_6$–$C_{14}$-aryl, a $C_6$–$C_{10}$-fluoroaryl, a $C_6$–$C_{10}$-aryloxy, a $C_2$–$C_{10}$-alkenyl, a $C_7$–$C_{40}$-arylalkyl, a $C_7$–$C_{40}$-alkylaryl or a $C_8$–$C_{40}$-arylalkenyl group, or two or more radicals $R^2$ and $R^3$ together with the atoms connecting them form one or more rings, $M^2$ are identical or different and are silicon, germanium or tin, and x is an integer from zero to 18, M is titanium, zirconium, hafnium, and X are identical or different and are each a halogen atom or a $C_1$–$C_{20}$-hydrocarbon radical such as $C_1$–$C_{10}$-alkyl.

Particular preference is given to preparing metallocenes of the formula II where $R^4$ and $R^{4'}$ are identical or different and are each a hydrogen atom, a halogen atom, $C_1$- to $C_{12}$-alkoxy, linear or branched $C_1$–$C_{15}$-alkyl, $C_4$–$C_{12}$-cycloalkyl, which can in turn bear $C_1$–$C_{12}$-alkyl as substituent, $C_1$–$C_{15}$-alkylalkenyl, $C_6$–$C_{24}$-aryl or arylalkyl where two adjacent radicals can form a $C_4$–$C_{24}$-ring system which can in turn be substituted, or an $R'_3Si$ group, where R' is a $C_1$–$C_{10}$-alkyl group, and $R^4$ and $R^{4'}$ can be cyclically connected to Z', Z' is $SiR^2R^3$ or a unit $Si-(CR^2R^3)_x-Si$ linking two metallocene fragments to one another, where $R^2$ and $R^3$ are identical or different and are each $C_1$–$C_{10}$-alkyl or $C_6$–$C_{10}$-aryl, and x is preferably 0, 2 or 6, M is zirconium and X is a chlorine atom.

Particular preference is given to preparing metallocenes of the formula II in which the two cyclopentadienyl groups are identical and are substituted. As substituents, the cyclopentadienyl groups preferably bear one or more $C_1$–$C_{30}$-hydrocarbon radicals. Examples of such cyclopentadienyl groups are 2-methylcyclopentadienyl, methyl-tert-butylcyclopentadienyl, tert-butylcyclopentadienyl, isopropylcyclopentadienyl, dimethylcyclopentadienyl, trimethylethylcyclopentadienyl, 5-phenylcyclopentadienyl, diphenylcyclopentadienyl, indenyl, 2-methylindenyl, 2-ethylindenyl, 3-methylindenyl, 3-tert-butylindenyl, 2-methyl-4phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl. Particular preference is given to indenyl derivatives. The indenyl derivatives preferably bear a $C_1$–$C_{10}$-hydrocarbon radical such as $C_1$–$C_{10}$-alkyl on the five-membered ring, particularly in the 2 position (adjacent to the bridge Z), and on the six-membered ring are either unsubstituted or bear one or more $C_1$–$C_{20}$-hydrocarbon radicals such as $C_1$–$C_{10}$-alkyl, $C_6$–$C_{20}$-aryl (e.g. phenyl or naphthyl) or two or more of the $C_1$–$C_{20}$-hydrocarbon radicals form a ring system.

Examples of metallocenes obtainable by the process of the invention, in particular those of the formula II, are:

dimethylsilanediylbis(2-methylindenyl)ZrCl$_2$;
dimethylsilanediylbisindenylZrCl$_2$;
dimethylsilanediylbis(2-methyl-4,5-benzoindenyl)ZrCl$_2$;
dimethylsilanediyl(2-methyl-4,5-benzoindenyl)(2-methylindenyl)ZrCl$_2$;
dimethylsilanediyl(2-methyl-4,5-benzoindenyl)(2-methyl-4-phenylindenyl)ZrCl$_2$;
dimethylsilanediyl(2-methylindenyl)(4-phenylindenyl)ZrCl$_2$;
dimethylsilanediylbis(2-methyl-4-phenylindenyl)ZrCl$_2$;
dimethylsilanediylbis(2-ethyl-4-phenylindenyl)ZrCl$_2$;
dimethylsilanediylbis(2-methyl-4,6-diisopropylindenyl)ZrCl$_2$;
dimethylsilanediylbis(2-methyl-4-naphthylindenyl)ZrCl$_2$;
dimethylsilanediylbis(2-ethyl-4-naphthylindenyl)ZrCl$_2$;
phenylmethylsilanediylbis(2-methylindenyl)ZrCl$_2$;
phenylmethylsilanediylbisindenylZrCl$_2$;
phenylmethylsilanediylbis(2-methyl-4,5-benzoindenyl)ZrCl$_2$;
phenylmethylsilanediyl(2-methyl-4,5-benzoindenyl)(2-methylindenyl)ZrCl$_2$;
phenylmethylsilanediyl(2-methyl-4,5-benzoindenyl)(2-methyl-4-phenylindenyl)ZrCl$_2$;
phenylmethylsilanediyl(2-methylindenyl)(4-phenylindenyl)ZrCl$_2$;
phenylmethylsilanediylbis(2-methyl-4-phenylindenyl)ZrCl$_2$;
phenylmethylsilanediylbis(2-methyl-4,6-diisopropylindenyl)ZrCl$_2$;
phenylmethylsilanediylbis(2-methyl-4naphthylindenyl)ZrCl$_2$;
diphenylsilanediylbis(2-methyl-4,5-benzoindenyl)ZrCl$_2$;
ethylenebis(2-methylindenyl)ZrCl$_2$;
ethylenebisindenylZrCl$_2$;
ethylenebis(2-methyl-4,5-benzoindenyl)ZrCl$_2$;
ethylene(2-methyl-4,5-benzoindenyl)(2-methylindenylZrCl$_2$;
ethylene(2-methyl-4,5-benzoindenyl)(2-methyl-4phenylindenyl)ZrCl$_2$;
ethylene(2-methylindenyl)(4-phenylindenyl)ZrCl$_2$;
ethylenebis(2-methyl-4-phenylindenyl)ZrCl$_2$;
ethylenebis(2-methyl-4,6-diisopropylindenyl)ZrCl$_2$;
ethylenebis(2-methyl-4-naphthylindenyl)ZrCl$_2$;
dimethylsilanediylbis(2,3,5-trimethylcyclopentadienyl)ZrCl$_2$;
1,6-bis[methylsilylbis(2-methyl-4-phenylindenyl)ZrCl$_2$]hexane;
1,6-bis[methylsilylbis(2-ethyl-4-phenylindenyl)ZrCl$_2$]hexane;
1,6-bis[methylsilylbis(2-methyl-4-naphthylindenyl)ZrCl$_2$]hexane;
1,6-bis[methylsilylbis(2-methyl-4,5-benzoindenyl)ZrCl$_2$]hexane;
1,6-bis[methylsilylbis(2-methyl-4,6-diisopropylindenyl)ZrCl$_2$]hexane;
1,2-bis[methylsilylbis(2-methyl-4-phenylindenyl)ZrCl$_2$]ethane;
1,2-bis[methylsilylbis(2-ethyl-4-phenylindenyl)ZrCl$_2$]ethane;
1,2-bis[methylsilylbis(2-methyl-4-naphthylindenyl)ZrCl$_2$]ethane;
1,2-bis[methylsilylbis(2-methyl-4,5-benzoindenyl)ZrCl$_2$]ethane;
1,2-bis[methylsilylbis(2-methyl-4,6-diisopropylindenyl)ZrCl$_2$]ethane.

In the process of the invention, use is preferably made of aprotic solvents such as benzene, toluene, chlorobenzene, carbon tetrachloride, methylene chloride, or di-($C_1$–$C_{10}$)-alkyl ethers like diethyl ether, methyl-tert.-butyl ether, diisopropyl ether and tetrahydrofuran. Particular preference is given to using a mixture of a nonpolar aprotic solvent (such as toluene or a non-polar di-($C_1$–$C_{10}$)-alkyl ether like methyl-tert.-butylether or diisopropyl ether) and a polar ether (such as tetrahydrofuran). The reaction is carried out in a temperature range from –70° to +100° C., preferably from –40° to +50° C., in particular from –20° to +30° C. The reaction can be carried out in a pressure range from 1 to 500 bar, preferably at atmospheric pressure.

To prepare bridged metallocenes, particularly those of the formula II, in which the two cyclopentadienyl ligands have identical substitution patterns, one equivalent of a cyclopentadiene derivative can be reacted, preferably in succession, with from 0.9 to 1.2 equivalents of a base, from 0.4 to 0.6 equivalent of a bridging reagent, from 0.9 to 1.2 equivalents of a base and from 0.3 to 0.7 equivalent of a metal compound.

To prepare metallocenes, particularly those of the formula II in which the two cyclopentadienyl ligands have different substitution patterns, preferably 0.5 equivalent of a cyclopentadiene A can be reacted with 0.4–0.6 equivalent of a base and subsequently with 0.9–1.2 equivalents of a bridging reagent. To this mixture can be added, preferably in succession, 0.5 equivalent of a cyclopentadienyl compound B which has a substitution pattern different from cyclopentadiene A, 0.9–1.2 equivalents of a base and 0.3–0.7 equivalent of a metal compound.

The in-situ process of the invention has the advantage that it can be carried out in a single reaction vessel and isolation of intermediates can be completely omitted. In addition, energy-consuming and time-consuming cooling and heating periods are unnecessary and a high reaction yield can be achieved.

The bridged metallocenes obtainable using the metallocene preparation process of the invention can, together with a cocatalyst, be used as highly active catalyst components, e.g. for the preparation of olefin polymers.

Olefins which can be polymerized are particularly those of the formula $R^a$—CH═CH—$R^b$, where $R^a$ and $R^b$ are identical or different and are each a hydrogen atom or a hydrocarbon radical having from 1 to 20 carbon atoms. $R^a$ and $R^b$ can also form a ring together with the carbon atoms connecting them. Examples of such olefins are ethylene, propylene, 1-butene, 1-hexene, 1-octene, 4methyl-1-pentene, 1,3-butadiene, isoprene, norbornene, dimethanooctahydronaphthalene or norbornadiene. In particular, propylene and ethylene can be homopolymerized, ethylene can be copolymerized with a $C_3$–$C_{20}$-olefin and/or a $C_4$–$C_{20}$-diene or ethylene can be copolymerized with a cycloolefin.

The polymerization can be a homopolymerization or a copolymerization and can be carried out in solution, in suspension or in the gas phase, continuously or batchwise, in one or more stages at a temperature of from 0° to 200° C., preferably from 30° to 100° C.

In principle, the cocatalyst in the polymerization can be any compound which, owing to its Lewis acidity, can convert the neutral metallocene into a cation and can stabilize the latter (labile coordination). Furthermore, the cocatalyst or the anion formed from it should undergo no further reactions with the cation formed (EP 427 697). The cocatalyst used is preferably an aluminum compound and/or boron compound.

Cocatalysts used are preferably aluminoxanes (EP-A 129 368), Polyhedron 1990, 9, 429). In place of or in addition to an aluminoxane, it is possible to use boron compounds, particularly those of the formulae $R_xNH_{4-x}BR'_4$, $R_xPH_{4-x}BR'_4$, $R_3CBR'_4$ or $BR'_3$, as cocatalyst. In these formulae, x is an integer from 1 to 4, preferably 3, the radicals R are identical or different, preferably identical and are $C_1$–$C_{10}$-alkyl, $C_6$–$C_{18}$-aryl or 2 radicals R together with the atoms connecting them form a ring, and the radicals R' are identical or different, preferably identical, and are $C_6$–$C_{18}$-alkyl or $C_6$–$C_{18}$-aryl which can be substituted by alkyl, haloalkyl or fluorine (EP-A 277 003, 277 004, 426 638, 427 697).

It is possible to preactivate the metallocene using a cocatalyst, in particular an aluminoxane, prior to use in the polymerization reaction. This can significantly increase the polymerization activity. The preactivation of the metallocene is preferably carried out in solution. The metallocene is here preferably dissolved in a solution of the aluminoxane in an inert hydrocarbon. Suitable inert hydrocarbons are aliphatic or aromatic hydrocarbons. Preference is given to using toluene.

To remove catalyst poisons present in the olefin, it is advantageous to carry out a purification using an aluminum compound, preferably an aluminum alkyl such as trimethylaluminum or triethylaluminum. This purification can be carried out either in the polymerization system itself, or the olefin is contacted with an aluminum compound prior to addition into the polymerization system and is subsequently separated off again.

As a molecular mass regulator and/or to increase the catalyst activity, hydrogen can be added in the polymerization process. This makes it possible to obtain low molecular weight polyolefins such as waxes.

The metallocene is preferably reacted with the cocatalyst outside the polymerization reactor in a separate step using a suitable solvent. Application to a support can be carried out during this step.

In the process, a prepolymerization can be carried out by means of the metallocene. The prepolymerization is preferably carried out using the (or one of the) olefin(s) used in the polymerization.

The catalyst used for the olefin polymerization can be supported. Application to a support enables, for example, the particle morphology of the polymer prepared to be controlled. The metallocene can here be reacted first with the support and subsequently with the cocatalyst, but the cocatalyst can also be first supported and subsequently reacted with the metallocene. It is also possible to support the reaction product of metallocene and cocatalyst. Suitable support materials are, for example, silica gels, aluminum oxides, solid aluminoxane or other inorganic support materials such as, for example, magnesium chloride. A polyolefin powder in finely divided form is also a suitable support material. The preparation of the supported cocatalyst can be carried out, for example, as described in EP 567 952.

Preferably, the cocatalyst, e.g. aluminoxane, is applied to a support such as, for example, silica gels, aluminum oxides, solid aluminoxane or other inorganic support materials such as, for example, magnesium chloride or else a polyolefin powder in finely divided form and then reacted with the metallocene.

If the polymerization is carried out as a suspension or solution polymerization, use is made of an inert solvent customary for the Ziegler low-pressure process. It is carried out, for example, in an aliphatic or cycloaliphatic hydrocarbon; examples of such hydrocarbons which may be mentioned are propane, butane, hexane, heptane, isooctane, cyclohexane and methylcyclohexane. It is also possible to use a petroleum fraction or hydrogenated diesel oil fraction. Toluene can also be used. Preference is given to carrying out the polymerization in the liquid monomer.

Use of hydrogen or increasing the polymerization temperature also enables the preparation of polyolefins of low molecular weight, such as waxes, whose hardness or melting point can be varied by means of the comonomer content. Selection of the polymerization process and the type(s) and amount(s) of comonomer allows the preparation of olefin copolymers having elastomeric properties, such as ethylene/propylene/1,4-hexadiene terpolymers.

The following Examples serve to illustrate the invention.

General: Preparation and handling of organometallic compounds were carried out with exclusion of air and moisture under a protective gas atmosphere (nitrogen, argon).

EXAMPLE 1

3.50 g (19.4 mmol) of 2-methyl-4,5-benzoindene are initially charged in 500 ml of toluene/25 ml of THF and admixed at room temperature with 7.46 ml (20 mmol) of butyllithium (2.68 molar in toluene). After stirring further for one hour, 1.25 g (9.7 mmol) of dimethyldichlorosilane is added and subsequently another 7.46 ml (20 mmol) of butyllithium are added at room temperature. At −40° C., 2.2 g (9.4 mmol) of zirconium tetrachloride are added in portions. The suspension is allowed to warm up to room temperature overnight, the suspension is filtered and the meso form is extracted with 50 ml of methylene chloride. The residue is further extracted with methylene chloride, the filtrate is evaporated and crystallized by storage at −30° C. This gives 1.75 g of rac-dimethylsilanediylbis(2-methyl-4,5-benzoindenyl)zirconium dichloride. Total yield: 31% of rac-dimethylsilanediylbis(2-methyl-4,5-benzoindenyl)zirconium dichloride (based on 2-methyl-4,5-benzoindene used).

EXAMPLE 2 (COMPARATIVE EXAMPLE)

a) 4.68 g (26 mmol) of 2-methyl-4,5-benzoindene are initially charged in 50 ml of THF and admixed at room temperature with 10.3 ml of a 2.5 molar butyllithium solution in hexane (26 mmol). The mixture is stirred for one hour at room temperature and is subsequently added at room temperature to a solution of 1.67 g (13 mmol) of dimethyldichlorosilane in 10 ml of THF. After the addition is complete, the mixture is stirred for 5 hours and subsequently poured into 100 ml of ice-water. The mixture is extracted a number of times with diethyl ether, the combined organic phases are dried over magnesium sulfate and the solvent is removed in vacuo. After chromatography over silica gel (hexane/ethyl acetate 20:1), 2.38 g (44%) of dimethylbis(2-methyl-4,5-benzoindenyl)silane are obtained.

b) 4.0 ml (10 mmol) of a 2.5 molar butyllithium solution in hexane are added at room temperature to a solution of 1.7 g (4 mmol) of dimethylbis(2-methyl-4,5-benzoindenyl)silane in 20 ml of THF. The mixture is stirred for 2 hours and the solvent is subsequently removed in vacuo. The residue is slurried in 10 ml of hexane, filtered off and dried. The dried dilithium salt is subsequently added at −78° C. to a suspension of 0.93 g (4 mmol) of zirconium tetrachloride in 25 ml of methylene chloride. The mixture is allowed to warm up to room temperature overnight, the yellow suspension is filtered off and the meso form is extracted with toluene. The residue is extracted with 40 ml of methylene chloride, the filtrate is evaporated and crystallized by storage at −30° C. This gives 0.97 g (42%) of rac-dimethylsilanediylbis(2-methyl-4,5-benzoindenyl)zirconium dichloride.

Total yield: 18.5% of rac-dimethylsilanediylbis(2-methyl-4,5-benzoindenyl)zirconium dichloride (based on 2-methyl-4,5-benzoindene used).

EXAMPLE 3

To a solution of 5.00 g (38.4 mmol) 2-methylidene in 300 ml methyl-tert.-butylether/5 ml tetryhydrofuran 14.9 ml (40 mmol) butyllithium (2.68 molar in toluene) was dropped at room temperature. Upon completion of the addition, the reaction mixture was stirred for 1 hour prior to treat with 2.50 g (19.4 mmol) dimethyldichlorsilane. The solution was treated with another amount of butyllithium (14.9 ml, 40 mmol) in toluene. At −20° C. 4.40 g (18.8 mmol) zirconiumtetrachloride was added in small portions. The suspension was slowly warmed to roomtemperature and stirred overnight. The suspension was filtrated and the residue was extracted with 65 ml methylenchloride to remove the mesoform. The residue was extracted totally with methylenchloride, the filtrat was concentracted and stored for crystallisation at −30° C. Filtration of the suspension afforded 2,74 g rac-Dimethylsilandiylbis(2-methylindenyl) zirconocen dichloride.

Total field: 30% rac-Dimethylsilandiylbis(2-methylindenyl)zirconocen dichloride (refer to used 2-methylidene).

EXAMPLE 4 (COMPARATIVE EXAMPLE)

a) 10 g (76,8 mmol) 2-methylidene are dissolved in 100 ml tetrahydrofuran and treated with 30.7 ml of a 2.5 molar butyllithium-solution in hexane (76.8 mmol) at roomtemperature. The mixture was stirred for 1 hour and then dropped to a solution of 4.93 g (38.4 mmol) of dimethyldichlorsilane in 40 ml tetrahydrofuran. After completion of the addition, the solution was stirred for 4 hours prior to add the solution to 250 ml icewater. The product was extracted with diethylether, the combined organic layers were dried over magnesiumsulfate and the solvent was removed in vacuo. After chromatographie over SiO₂ (hexane/ethylacetate 35:1) 6.07 g (50%) dietmethylbis (2-methylindenyl)silane were afforded.

b) 15.3 ml (38.4 mmol) of a 2.5 molar solution of buthyllithium hexane were added to a solution of 6.07 g (19.2 mmol) dimethylbis(2-methylindenyl)-silane in 80 ml tetrahydrofuran. The mixture was refluxed for 2 hours prior to solvent evaporation. The residue was suspended in 30 ml of hexane, the suspension was filtrated and the dilithiocompound was dried in vacuo. The dilithio-compound was then added to a suspension of 4.47 g (19.2 mmol) zirconiumtetrachloride in 50 ml metylenchloride at −78° C. The suspension was slowly warmed to room temperature and stirred over night. The suspension was filtrated and the meso-compound was removed by extraction with toluene. The residue was extracted with 70 ml methylenchloride, the filtrat was concentrated and stored for crystallisation at −30° C. Filtration of the suspension afforded 3,20 g (35%) rac-dimethylsilandiylbis(2-methylindenyl)zirconocen dichloride.

Total yield: 17.5% rac-Dimethylsilandiylbis(2-methylindenyl)zirconocen dichloride (refer to used 2-methylindene).

We claim:

1. An in-situ process for preparing a bridged metallocene, which comprises reacting with one another in a single reaction vessel, a substituted cyclopentadiene, at least one base, at least one bridging reagent, and at least one metal component.

2. The in-situ process as claimed in claim 1, wherein the following steps are carried out in succession:
   a) the substituted cyclopentadiene is deprotonated with a base and then reacted with a bridging reagent, which is proceeded by
   b) a subsequent addition of a base and then the addition of a metal component.

3. The in-situ process as claimed in claim 1 for preparing a bridged metallocene having identical cyclopentadienyl ligands, wherein the substituted cyclopentadiene is deprotonated with a base and then reacted with a bridging reagent to give a bridged ligand system which is subsequently, without isolation of the bridged ligand system, again deprotonated with a base and reacted with a metal component to give a bridged metallocene having identical cyclopentadienyl ligands.

4. The in-situ process as claimed in claim 1, wherein the substituted cyclopentadiene is a compound of the formula Ia

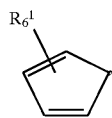

where the radicals

R$^1$ are identical or different and are each a hydrogen atom, a halogen atom, a C$_1$–C$_{30}$-hydrocarbon group, a C$_1$–C$_{15}$-alkylalkenyl, C$_6$–C$_{24}$-aryl or C$_7$–C$_{30}$-arylalkyl group, or a C$_1$–C$_{12}$-alkoxy group, or two or more adjacent radicals R$^1$ can form a C$_4$–C$_{24}$-ring system which in turn can be substituted, or an R'$_3$Si group where R' are identical or different and are each a hydrogen atom, a halogen atom, a C$_1$–C$_{20}$-alkyl, a C$_1$–C$_{10}$-fluoroalkyl, a C$_1$–C$_{10}$-alkoxy, a C$_6$–C$_{14}$-aryl, a C$_6$–C$_{10}$-fluoroaryl, a C$_6$–C$_{10}$-aryloxy, a C$_2$–C$_{10}$-alkenyl, a C$_7$–C$_{40}$-arylalkyl, a C$_7$–C$_{40}$-alkylaryl or a C$_8$–C$_{40}$-arylalkenyl group, and at least two radicals R$^1$ are hydrogen atoms and at least one radical R$^1$ is different from a hydrogen atom.

5. The in-situ process as claimed in claim 1, which further comprises reacting an unsubstituted or substituted cyclopentadienyl compound which has a substitution pattern different from the cyclopentadiene.

6. The in-situ process as claimed in claim 2, wherein after step a) but before step b), an unsubstituted or substituted cyclopentadienyl compound which has a substitution pattern different from the cyclopentadiene is added to give a bridged metallocene having different cyclopentadienyl ligands.

7. The in-situ process as claimed in claim 5, wherein the cyclopentadienyl compound has the formula 1b

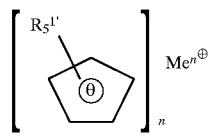

where the radicals

R1' are identical or different and are each a hydrogen atom, a halogen atom, a C$_1$–C$_{30}$-hydrocarbon group, a C$_1$–C$_{15}$-alkylalkenyl, C$_6$–C$_{24}$-aryl or C$_7$–C$_{30}$-arylalkyl group, or a C$_1$–C$_{12}$-alkoxy group, or two or more adjacent radicals R1' can form a C$_4$–C$_{24}$-ring system which can in turn be substituted, or an R'$_3$Si group, where R' can be identical or different and are each a hydrogen atom, a halogen atom, a C$_1$–C$_{20}$-alkyl, a C$_1$–C$_{10}$-fluoroalkyl, a C$_1$–C$_{10}$-alkoxy, a C$_6$–C$_{14}$-aryl, a C$_6$–C$_{10}$-fluoroaryl, a C$_6$–C$_{10}$-aryloxy, a C$_2$–C$_{10}$-alkenyl, a C$_7$–C$_{40}$-arylalkyl, a C$_7$–C$_{40}$-alkylaryl or a C$_8$–C$_{40}$-arylalkenyl group, where at least one radical R1' is a hydrogen atom and Me is an n-valent metal and n is equal to 1 or 2.

8. The in-situ process as claimed in claim 7, wherein Me is lithium, sodium, potassium or magnesium.

9. The in-situ process as claimed in claim 1, wherein the bridging reagents are compounds of the formula ZY$_n$, where Z is

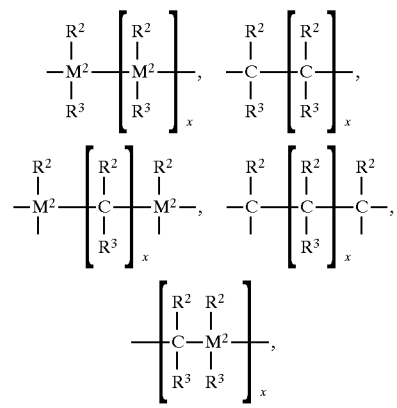

=BR$^2$, =AlR$^2$, —Ge—, —O—, —S—, =SO, =SO$_2$, =NR$^2$, =CO, =PR$^2$ or =P(O)R$^2$, where R$^2$ and R$^3$ are identical or different and are each a hydrogen atom, a halogen atom, a C$_1$–C$_{20}$-alkyl, a C$_1$–C$_{10}$-fluoroalkyl, a C$_1$–C$_{10}$-alkoxy, a C$_6$–C$_{14}$-aryl, a C$_6$–C$_{10}$-fluoroaryl, a C$_6$–C$_{10}$-aryloxy, a C$_2$–C$_{10}$-alkenyl, a C$_7$–C$_{40}$-arylalkyl, a C$_7$–C$_{40}$-alkylaryl or a C$_8$–C$_{40}$-arylalkenyl group, or two or more radicals R$^2$ and R$^3$ together with the atoms connecting them form one or more rings, M$^2$ are identical or different and are each silicon, germanium or tin, x is an integer from zero to 18, Y are identical or different and are each a leaving group such as a halogen atom or a tosylate, and n is equal to 2 or 4.

10. The in-situ process as claimed in claim 1, wherein the bases used are alkyl-alkali metal compounds.

11. The in-situ process as claimed in claim 10, wherein the alkyl-alkali metal compounds are alkyllithium compounds.

12. The in-situ process as claimed in claim 1, wherein the metal components are compounds of the formula Mx$_p$, where M is a metal of group IIIb, IVb, Vb, VIb of the Periodic Table of the Elements, X is a halogen atom or an NR$^{11}{}_2$ group, where R$^{11}$ are identical or different and are each a hydrogen atom, a halogen atom, or a C$_1$–C$_{40}$-carbon-containing group, and p is an integer from 2 to 6.

13. The in-situ process as claimed in claim 12, wherein the C$_1$–C$_{40}$-carbon-containing group is selected from the group consisting of a C$_1$–C$_{20}$-alkyl, a C$_1$–C$_{10}$-fluoroalkyl, a C$_1$–C$_{10}$-alkoxy, a C$_6$–C$_{14}$-aryl, a C$_6$–C$_{10}$-fluoroaryl, a C$_6$–C$_{10}$-aryloxy, a C$_2$–C$_{10}$-alkenyl, a C$_7$–C$_{40}$arylalkyl, a C$_7$–C$_{40}$-alkylaryl or a C$_8$–C$_{40}$-arylalkenyl group.

* * * * *